United States Patent [19]

Trewyn et al.

[11] Patent Number: 4,687,733
[45] Date of Patent: Aug. 18, 1987

[54] EARLY CANCER DETECTION METHOD

[75] Inventors: Ronald W. Trewyn, Upper Arlington; Steven M. D'Ambrosio, Columbus, both of Ohio

[73] Assignee: Ohio State University, Columbus, Ohio

[21] Appl. No.: 575,262

[22] Filed: Jan. 30, 1984

[51] Int. Cl.[4] ............................................. G01N 33/53
[52] U.S. Cl. ........................................ 435/7; 436/536; 436/537; 436/538; 436/539; 436/540; 436/541; 436/542; 436/547; 436/548; 436/804; 436/813; 935/100; 935/102; 935/104; 935/106; 935/108
[58] Field of Search .................... 435/7; 436/536–542, 436/547, 548, 804, 813; 935/100, 102, 104, 106, 108

[56] References Cited

PUBLICATIONS

Terry et al., Carcinoembryonic Antigen: Characterization and Clinical Applications, Transplant Rev., 20: 100–129, 1974.

Weissmann et al., The Purine Bases of Human Urine. II. Semiquantitative Estimation and Isotope Incorporation. J.Biol. Chem. 224: 423–434, 1957.

Mandel et al., The Biosynthesis of Methylated Bases in Ribonucleic Acid. Biochemistry 2: 555–560, 1963.

Mandel et al., Origin of Urinary Methylated Purines. Nature 209: 586–588, 1966.

Gehrke et al., Quantitative High-Performance Liquid Chromatography of Nucleosides in Biological Materials. J. Chromatogr. 150: 455–475, 1978.

Hartwick et al., Identification and Quantitation of Nucleosides, Bases, and Other UV-Absorbing Compounds in Serum, Using Reversed Phase High-Performance Liquid Chromatography. J. Chromatogr. 186: 647–658, 1979.

Speer et al., tRNA Breakdown Products as Markers for Cancer. Cancer 44: 2120–2123, 1979.

Trewyn et al., Elevated Nucleoside Execretion by Patients with Nasopharyngeal Carcinoma: Preliminary Diagnostic/Prognostic Evaluations. Cancer 49: 2513–2517, 1982.

Heldman et al., Differential Execretion of Modified Nucleosides in Adult Acute Leukemia. Blood 61: 291–296, 1983.

Heldman et al., Urinary Excretion of *Modified Nucleosides* in Chronic Myelogenous Leukemia. *J. Lab. Clin. Med. 101:* 783–792, 1983.

Heldman et al., Relationship of Urinary Excretion of Modified Nucleosides to Disease Status in Childhood Acute Lymphoblastic Leukemia, J Natl. Cancer Inst. 71: 269–273, 1983.

Levine et al., Serum Levels of $N^2,N^2$-Dimethylguanosine and Pseudouridine as Determined by Radioimmunoassay for Patients with Malignancy. J. Natl. Cancer Inst. 54: 341–343, 1975.

Vold, Radioimmunoassays for the Modified Nucleosides N-[9-($\beta$-D-Ribofuranosyl) Purin-6-Ylcarbamoyl]-L-Threonine and 2-Methylthioadenosine. Nucleic Acids Res. 7: 193–204, 1979.

Vold et al., Urine Levels of N-[9-($\beta$-D-Ribofuranosyl) Purin-6-Ylcarbamoyl]-L-Threonine, $N^6$-($\Delta^2$-Isopentenyl) Adenosine, and 2'-O-Methylguanosine as Determined by Radioimmunoassay for Normal Subjects and Cancer Patients. Cancer Res. 42: 5265–5269, 1982.

Woodsworth et al., Characterization of Monoclonal Antibodies Specific for Isopentenyl Adenosine Derivatives Occurring in Transfer RNA. Biochem. Biophys. Res. Commun. 114: 791–796, 1983.

(List continued on next page.)

*Primary Examiner*—Christine M. Nucker
*Attorney, Agent, or Firm*—Emch, Schaffer, Schaub & Porcello Co.

[57] ABSTRACT

The invention relates to a method of testing for the presence of cancer. An antibody is produced which contains antibodies specific to a modified nucleoside component. The antibody is admixed with a body fluid drawn from a subject mammal. An immunoassay is performed on the admixture to quantify an amount of cancer associated nucleoside present in the fluid and reactive with the antibody.

19 Claims, 9 Drawing Figures

PUBLICATIONS

Erlanger, B. F., et al., Antibodies Specific for Ribonucleosides and Ribonucleotides and Their Reation with DNA, Proc. Natl. Acad. Sci. U.S., 52:68–74 (1964).

Inouye, H., et al., Anti-Inosine Antibodies, Biochem. Biophys. Acta., 240; 596–603 (1971).

Farr, R. S., A Quantitative Immunochemical Measure of the Primary Interaction Between I*BSA and Antibody, J. Infec. Dis. 103: 239–262 (1958).

Muller, R., Calculation of Average Antibody Affinity in Antihapten Sera from Data Obtained by Competitive Radioimmunoassay, J. Immunol Meth., 34: 345–352 (1980).

Fishbein, A., et al., Urinary Excretion of Modified Nucleosides in Patients with Malignant Mesothelioma, Cancer Research 43, 2971–2974, (Jun. 1983).

Waalkes, T. P., et al., Urinary Excretion by Cancer Patients of the Nucleosides $N^2$, $N^2$-Dimethylguanosine, 1-Methylinosine, and Pseudouridine, J. Natl. Cancer Inst., 51: 271–274, 1973.

Tormey, D. C., et al., Biological Markers in Breast Carcinoma-Clinical Correlations with Pseudouridine, $N^2$, $N^2$-Dimethylguanosine and 1-Methylinosine, Journal of Surgical Oncology 14:267–273 (1980).

Rasmuson, T., et al., Evaluation of Carcinoembryonic Antigen, Tissue Polypeptide Antigen, Placental Alkaline Phosphatase, and Modified Nucleosides as Biological Markers in Malignant Lymphomas, Resent Results in Cancer Research, vol. 84, Springer-Verlag Berlin, Heidelberg, 1983.

Gehrke, C. W., et al., Patterns of Urinary Excretion of Modified Nucleosides, Cancer Research 39, 1150–1153, Apr. 1979.

Borek, E., et al., New Applications of Urinary Nucleoside Markers, Recent Results in Cancer Research, vol. 84, Springer-Verlag Berlin, Heidelberg, 1983.

Clark, I., et al., Comparison of Urinary Modified Nucleosides and Bases in Rats with Hepatomas and Nephroblastomas, Recent Results in Cancer Research, vol. 84, Springer-Verlag Berlin, Heidelberg, 1983.

Waalkes, T. P., et al., The Urinary Excretion of Nucleosides of Ribonucleic Acid by Patients with Advance Cancer, Cancer 36: 390–398, 1975.

Hartwick, R. A., et al., Identification and Quantitation of Nucleosides, Bases and Other UV-Absorbing Compounds in Serum, Using Reversed Phase High-Performance Liquid Chromatography, J. Chromatog., 186: 659–676, 1979.

Thomale, J., et al., Elevated Urinary Excretion of RNA Catabolites as an Early Signal of Tumor Development in Mice, Cancer Letters, 15: 149–159, 1982.

Waalkes, T. P., et al., Modified Ribonucleosides as Biological Markers for Patients with Small Cell Carcinoma of the Lung, Eur. J. Cancer Clin. Oncol. vol. 18, No. 12, 1267–1274, 1982.

Borek, E., et al., Urinary Nucleic Acid Breakdown Products as Markers for Trophoblastic Diseases, Am. J. Obstet. Gynecol. 146: 906, 1983.

Fink, K., et al., Urinary Purines and Pyrimidines in Normal and Leukemic Subjects, Archives of Biochemistry and Biophysics, 126, 27–33, 1968.

Weissmann, B., et al., The Purine Bases of Human Urine, I. Separation and Identification, J. Biol. Chem. 224: 407–421 (1956).

Yu, T. F., et al., On the Biosynthesis of Uric Acid from Glycine-$N^{15}$ in Primary and Secondary Polycythemia, Amer. J. of Med. vol. 21(6): 901–917, Dec. 1956.

Heldman et al., Urinary Excretion of Modified Nucleosides in Chronic Myelogenous Leukemia. Proc. Amer. Soc. Clin. Oncology 1:6, 1982.

Heldman et al., Relationship of Modified Nucleoside Excretion to Disease Status in Childhood Acute Lymphoblastic Leukemia, Blood 60: 128a, 1982.

Heldman et al., Differential Excretion of Modified Nucleosides in Adult Acute Leukemia, Blood 60: 129a, 1982.

Lutter et al., Elevated Excretion of Modified Nucleosides in Non-Hodgkins Lymphomas, Blood 60: 147a, 1982.

Trewyn et al., Alterations in tRNA Metabolism as Markers of Neoplastic Transformation In: Biochemical and Biological Markers of Neoplastic Transformation (P. Chandra, ed) pp. 263–276, Plenum Publishing Corp., New York, 1983.

Age-Adjusted Nucleoside Excretion by Children with ALL[a]

| Patient | Bone Marrow % Blasts | Nucleoside Excretion (nmoles/μmole creatinine) | | | | |
|---|---|---|---|---|---|---|
| | | $m^1I$ | $m_2^2G$ | $m^1G$ | Ψ | PCNR |
| 1a. | 93 | (4.26)[b] | 3.85 | 1.41 | (42.26) | (2.87) |
| b. | 0 | 2.00 | 3.50 | 1.97 | 39.30 | 1.40 |
| 2. | 2 | 1.97 | 2.41 | (2.92) | (43.18) | (3.90) |
| 3. | 99 | (5.32) | (4.68) | (2.49) | 34.41 | 0.93 |
| 4. | 9 | (2.97) | 3.27 | 2.32 | 40.94 | (2.37) |
| 5. | 81 | (2.99) | 3.65 | 2.22 | 39.47 | 1.33 |
| 6. | 0 | 2.41 | 3.77 | 2.09 | 36.41 | (2.12) |
| 7. | 2 | 2.72 | 3.05 | (3.03) | 36.40 | 1.49 |
| 8. | 3 | 2.30 | 2.46 | 1.62 | (41.12) | 1.75 |
| 9. | 0.5 | 2.14 | 2.85 | 1.48 | 32.00 | 1.15 |
| 10. | 1 | 1.97 | 1.42 | 1.09 | (42.44) | 1.34 |
| 11a. | 9 | 2.30 | 2.53 | 2.10 | 35.44 | 0.91 |
| b. | 0 | 1.76 | 1.84 | 1.50 | 35.11 | 1.23 |
| 12. | 1 | 1.93 | 2.60 | 1.39 | 37.03 | (1.87) |
| 13. | 0 | 2.14 | 2.43 | 1.75 | 34.64 | 1.22 |
| 14. | 0 | 2.07 | 2.69 | 1.79 | 36.60 | (2.54) |
| 15. | 1 | 2.16 | 2.78 | 1.78 | 35.63 | 0.80 |
| 16. | 78 | (5.32) | (6.69) | (4.15) | (62.56) | (3.54) |
| 17. | 39 | (3.13) | 3.60 | 2.26 | (41.69) | 1.72 |
| 18. | 0 | 2.69 | 3.10 | 1.88 | 37.50 | 1.14 |
| 19. | 0 | 1.85 | 2.43 | 1.23 | 35.80 | 1.79 |
| 20. | 84 | (4.93) | 3.63 | (5.47) | (48.02) | (2.29) |
| 21. | 2 | 2.49 | 2.98 | 1.86 | 39.91 | 1.34 |
| 22. | 29 | (3.52) | (4.27) | (2.74) | (43.10) | (2.62) |
| 23. | 2 | 2.52 | 3.13 | 2.09 | 34.64 | 1.40 |
| 24. | 70 | (5.25) | (5.27) | (2.72) | (49.44) | (1.91) |

[a] Normal age-adjusted mean ± standard deviation values for the fifteen healthy children expressed as nmoles nucleoside/μmole creatinine were: $m^1I$, 2.38 ± 0.28; $m_2^2G$, 3.27 ± 0.40; $m^1G$, 1.83 ± 0.29; Ψ 33.19 ± 3.96; PCNR, 1.29 ± 0.29. The coefficients of variation ranged from 12 to 22%.

[b] Patient age-adjusted nucleoside excretion values greater than two standard deviations above the normal control values are indicated in parentheses.

FIG. 4

Urinary nucleoside excretion by control subjects*

| Nucleoside | Excretion Level (nmoles/μmole creatinine)† | RSD‡ |
|---|---|---|
| Pseudouridine | 20.89 ± 4.32 | 20.7 |
| 1-Methyladenosine | 2.15 ± 0.46 | 21.4 |
| PCNR | 0.68 ± 0.16 | 23.5 |
| 1-Methylinosine | 1.20 ± 0.24 | 20.0 |
| 1-Methylguanosine | 0.71 ± 0.16 | 22.5 |
| Adenosine § | 0.29 ± 0.09 | 31.0 |
| $N^2,N^2$-Dimethylguanosine | 1.25 ± 0.30 | 24.0 |

*Twenty-four healthy adults, aged 20-50, 14 males and 10 females.

†Mean ± standard deviation.

‡% RSD, Percent relative standard deviation.

§Values for adenosine are based on only 17 subjects because adenosine was not quantitated in some of the more dilute urine specimens.

FIG. 6

EARLY CANCER DETECTION METHOD

Cancer is one of the most significant causes of death in the world accounting for approximately 20% of all deaths. The disease can affect persons of all ages, background, and socio-economic status. Cancer is an extremely expensive health problem, costing billions of dollars for treatment and loss in productivity annually.

It has been estimated that early detection of cancer could result in a tremendous savings of life, health care costs, and productivity. The Pap test, for example, which involves the microscopic examination of cells from the uterous has aided in the early detection of uterine cancer, and has thereby contributed to the significant decrease in mortality from this disease.

The Hemoccult test which detects occult blood in the stool may offer an early warning of colon-rectal cancer. However, it is too early to tell whether this test will increase the survival rate for this disease which has remained fairly constant for many years.

Other tests involve the use of cancer markers such as carcinoembryonic antigen (CEA), a glycoprotein found in the blood of some cancer patients. See, Terry et al., Carcinoembryonic Antigen: characterization and clinical applications, Transplant Rev., 20: 100-129, 1974. However, the CEA assay lacks specificity, and as with other tests currently available, its usefulness appears to be limited to the management of only a few forms of cancer. Therefore, additional means of early cancer detection are required.

It is known that patients with a variety of malignant neoplasms excrete elevated levels of methylated purines and pyrimidines as well as other modified bases and nucleosides (Weissmann et al., The purine bases of human urine. II. semiquantitative estimation and isotope incorporation. J. Biol. Chem. 224: 423-434, 1957). The origin of these compounds was obscure until the discovery of the modification of tRNA in cells (Mandel and Borek, The biosynthesis of methylated bases in ribonucleic acid. Biochemistry 2: 555-560, 1963). The excretory products are predominantly minor components of tRNA which originate from the breakdown of the cellular macromolecules. (Mandel et al., Origin of urinary methylated purines. Nature 209: 586-588, 1966). The normal turnover of tRNA generates sufficient amounts of the modified components so that they can be quantitated in urine or serum. (Gehrke et al., Quantitative high-performance liquid chromatography of nucleosides in biological materials. J. Chromatogr. 150: 455-475, 1978; Hartwick et al., Identification and quantitation of nucleosides, bases, and other UV-absorbing compounds in serum, using reversed-phase high-performance liquid chromatography. J. Chromatogr. 186: 647-658, 1979). However, cancer patients excrete highly elevated levels of these modified bases and nucleosides, so monitoring the amounts of these compounds in urine or serum offers a valuable biological marker for cancer (Speer et al., tRNA breakdown products as markers for cancer. Cancer 44: 2120-2123, 1979). However, current methodologies for detection of these compounds involve complex and expensive equipment and processes.

Therefore, there is a need for a simpler, less costly yet highly reliable method for monitoring the amounts of these compounds in urine or serum such that these compounds can be used routinely as valuable biological markers for cancer.

This invention provides raising monoclonal and polyclonal antibodies against 1-methylinosine and other 1-methyl purine ribonucleosides (e.g. 1-methylguanosine) for use in immunoassay procedures for cancer screening and monitoring. The primary method employed is an enzyme-linked immunosorbant assay which does not require the use of radioisotopes. A simple color change (absorbance at 405 nm) monitored with an appropriate instrument allows 1-methylinosine to be quantitated from body fluids, such as urine or serum. In urine, the quantitation is relative to the urine creatinine content (i.e., nmoles 1-methylinosine per umole creatinine), while quantitation in serum is based on volume (i.e., nmoles, or pmoles 1-methylinosine per ml of serum). Alternative immunoassay methods utilized are an ultrasensitive enzyme-linked radioimmune assay and the standard radioimmunoassay.

FIG. 4 is a table showing age-adjusted nucleoside excretion by children with ALL.

FIG. 6 is a table showing urinary nucleoside excretion by control subjects.

Various nucleosides are described herein. The correlation between full names and abbreviations is:

$m^1I$ = 1-methylinosine
$m^1G$ = 1-methylguanosine
$\Psi$ = pseudouridine
$m^1A$ = 1-methyladenosine
$m^5C$ = 5-methylcytidine
G = guanosine
A = adenosine
PCNR = 2-pyridone-5-carboxamide-N'-ribofuranoside
$m_2^2G$ = $N^2$, $N^2$-dimethylguanosine
IS = internal standard (deoxyadenosine)

Various other abbreviations are used herein. The correlation between full names and abbreviations is:
CEA = carcinoembryonic antigen
tRNA = transfer ribonucleic acid
HPLC = high performance liquid chromatography
NAD = nicotinamide adenine dinucleotide
ALL = acute lymphoblastic leukemia
AML = acute myelogenous leukemia CML = chronic myelogenous leukemia
BSA = bovine serum albumin
KLH = keyhole limpet hemocyanin
PBS = phosphate buffered saline
ELISA = enzyme linked immunosorbant assay
BBOT = 2,5-bis-(5-tert-butylbenzoxazolyl-thiophene)
FCS = fetal calf serum
HAT = Hypoxanthine, aminopterin, thymidine
r = correlation coefficient
USERIA = ultrasensitive enzyme linked radioimmune assay
RIA = radioimmunoassay
1-methylinosine has the formula:

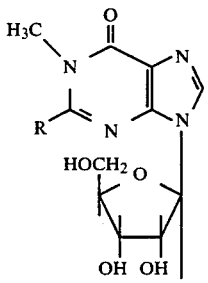

wherein R=H
1-methylguanosine has the formula:

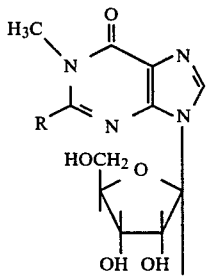

wherein R=NH$_2$

Figure 1:
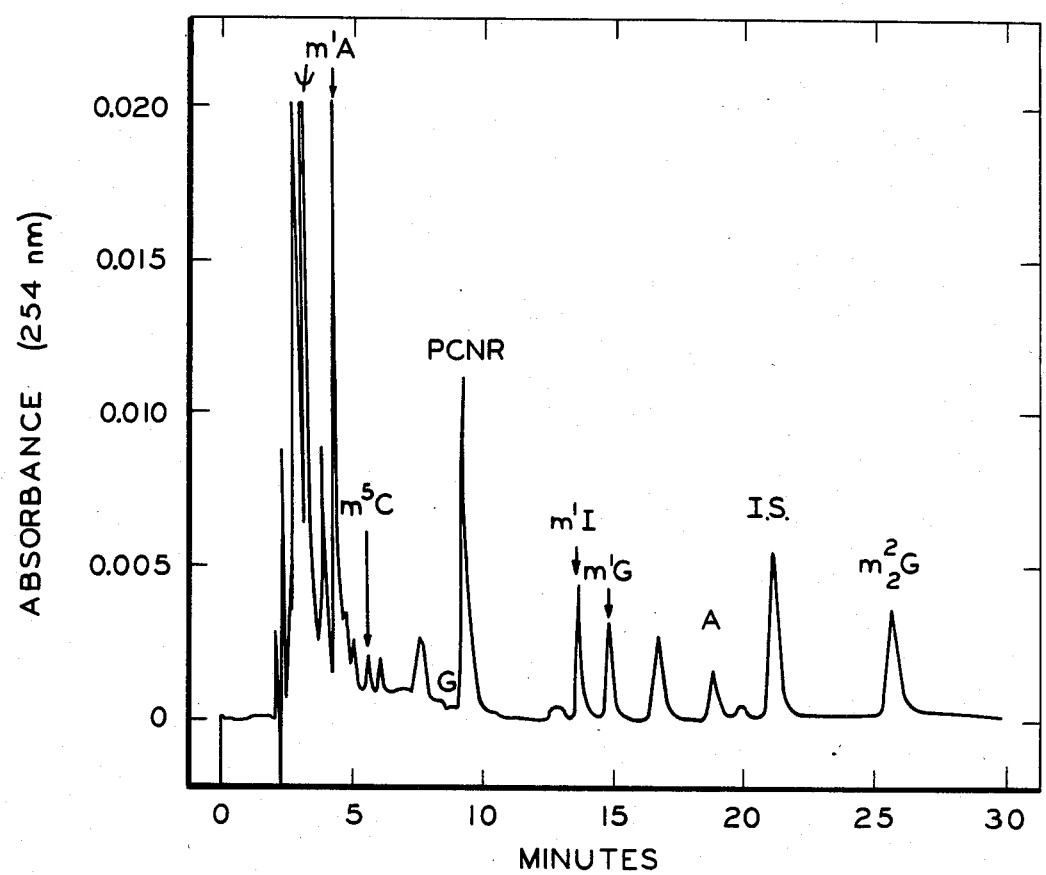
FIG. 1 is a graph showing the reversed-phase high performance liquid chromatography separation of nucleosides in control urine.

Modified urinary nucleosides are useful for diagnostic and prognostic evaluations of cancer and also for disease management. Trewyn et al., (Elevated nucleoside execretion by patients with nasopharyngeal carcinoma: Preliminary diagnostic/prognostic evaluations. Cancer 49: 2513-2517, 1982) described the separation of nucleosides in urine samples of adult male controls in apparent good health. FIG. 1 presents a high performance liquid chromatography (HPLC) separation of nucleosides in control urine. Not all of the peaks in normal urine have been identified, and the peaks at 7.6 and 16.7 minutes contain more than one component. However, pseudouridine, 1-methyladenosine, 5-methylcytidine, guanosine, 2-pyridone-5-carboxamide-N'-ribofuranoside (a breakdown product of NAD), (Speer, et al., 1979) 1-methylinosine, 1-methylguanosine, adenosine, and N$^2$, N$^2$-dimethylguanosine are resolved.

Figure 2:
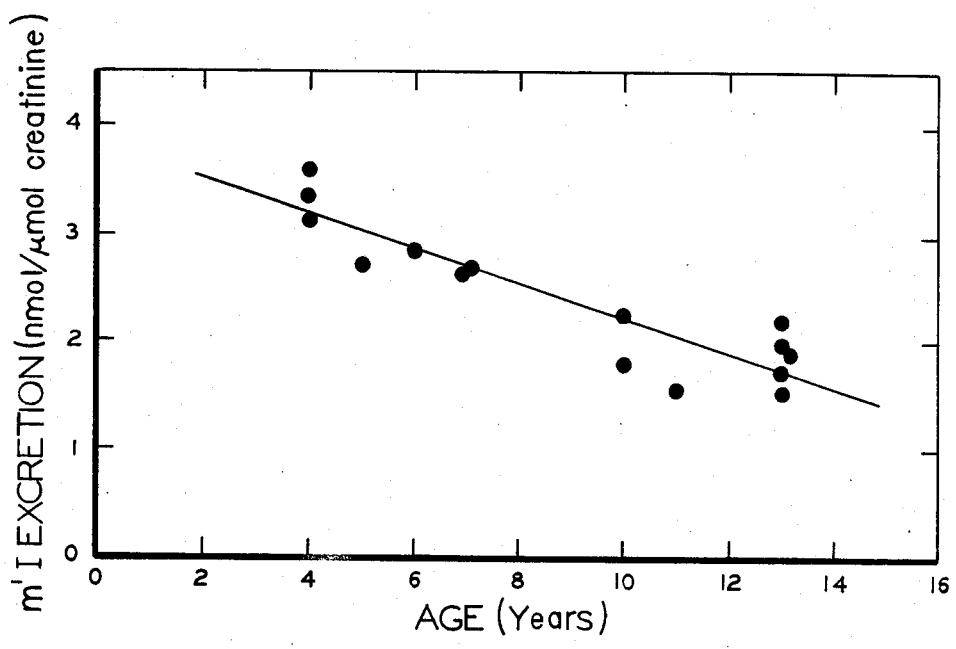
FIG. 2 is a graph showing excretion of 1-methylinosine by normal healthy children.

1-methylinosine, specifically, is a most useful modified nucleoside as a cancer marker, especially for leukemias. The urinary excretion of 1-methylinosine correlates more closely with bone marrow tumor burden (r=0.90) than does the most common screening method of quantitating malignant cells in the peripheral blood (r=0.47) (Heldman et al., Relationship of modified mucleoside excretion to disease status in childhood acute lymphoblastic leukemia. J. Natl. Cancer Inst. 71: 269-273, 1983). In this study the urinary excretion levels of m$^1$I, m$_2^2$G, m$^1$G, Ψ, and PCNR were quantitated relative to the urine creatinine concentration for 15 normal healthy children. The excretion level of each nucleoside was found not to vary with the sex of the subject. As shown in FIG. 2, m$^1$I excretion demonstrated a negative linear relationship with age (r=−0.91) such that excretion of m$^1$I in nmol m$^1$I/μ-mol creatinine decreased 0.16 for each 1-year increase in age.

Figure 3:
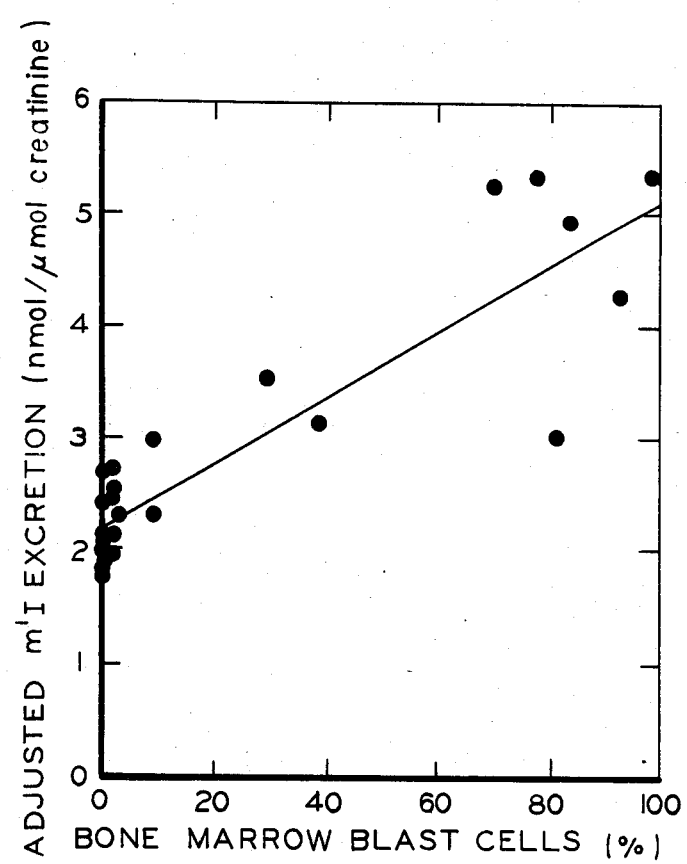
FIG. 3 is a graph showing excretion of 1-methylinosine relative to urine creatinine concentration as a function of percentage of lymphoblasts in bone marrow of patients with childhood acute lymphoblastic leukemia (ALL).

As shown in FIG. 3, a positive linear relationship between m$^1$I excretion and the percentage of blast cells in the patients' bone marrow aspirates was also established; the correlation was excellent (r=0.90). The actual m$^1$I excretion values for each of these leukemia patients are presented in FIG. 4, where they can be compared directly to the percentage of immature cells in the bone marrow aspirates. All patients in remission (<5% blast cells in their bone marrows) excreted m$^1$I in the normal range. With one exception, all patients in relapse (>5% blasts) excreted m$^1$I at significantly elevated levels. Only patient #11 in relapse (9% blasts) failed to yield an elevated m$^1$I value. However, the m$^1$I value for patient #11 when in remission (0% blast cells) was the lowest of the patient group, and, in fact, it was the only m$^1$I excretion value that was greater than two standard deviations below the normal controls. Therefore, relative to his own remission value (1.76 nmol m$^1$I/μmol creatinine), patient #11 was excreting m$^1$I at an increased level when in relapse (2.30 mol m$^1$I/μmol creatinine). Comparable increases were also observed for m$_2^2$G and m$^1$G with this patient, as shown in FIG. 4.

The complete data for the other nucleosides are also presented in FIG. 4. The excretion levels of the four nucleosides other than m$^1$I did not show as close a relationship to percentage of blast cells; the r's for m$_2^2$G, m$^1$G, Ψ, and PCNR were 0.78, 0.51, 0.54, and 0.25, respectively. For comparison, the r for the absolute blast cell count in the peripheral blood to the percentage of blasts in the bone marrow was 0.47. Therefore, the non-invasive 1-methylinosine determination serves as a desirable, specific alternative to bone marrow determinations in following disease activity in these patients.

At original diagnosis of leukemia in adults, 1-methylinosine allows one to distinguish among acute myelogenous leukemia, acute lymphoblastic leukemia, and chronic myelogenous leukemia in difficult cases (Heldman et al., Differential execretion of modified nucleosides in adult acute leukemia. Blood 61: 291-296, 1983; Heldman et al., Urinary excretion of modified nucleosides in chronic myelogenous leukemia. J. Lab. Clin. Med. 101: 783-792, 1983). 1-methylinosine is indicative of stable or active disease, and is diagnostic of early relapse. Current data indicates that the same nucleoside may alternatively be a diagnostic and/or prognostic marker for lymphomas and lung cancer.

Elevation of urinary excretion of modified nucleosides has been demonstrated in patients with various malignancies. Heldman et al. J. Lab. Clin. Med. 101, (1983) has recently shown that nucleoside excretion is a marker of disease status in chronic myelogenous leukemia (CML). Elevated nucleoside excretion is an early indicator of acceleration in that hematologic malignancy. Modified nucleosides are primarily components of transfer RNA (tRNA) that are excreted when the ribonucleic acid is catabolized.

Figure 5:
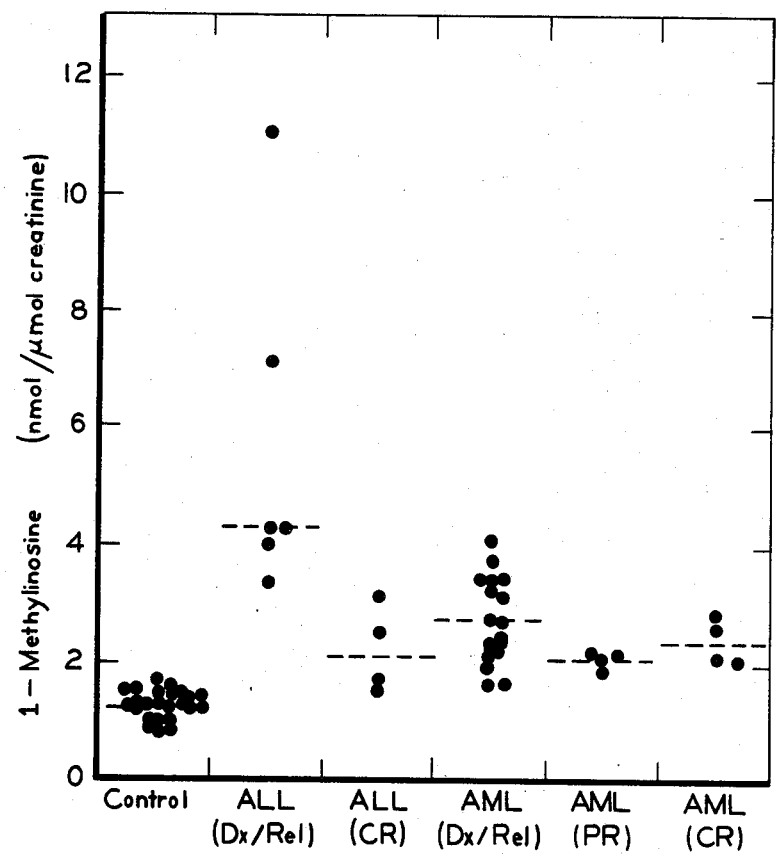
FIG. 5 is a graph showing the urinary excretion of 1-methylinosine relative to creatinine concentration in healthy control subjects and subjects having various leukemias, either at initial diagnosis or relapse or in complete remission.

Urinary excretion of modified nucleosides from patients with acute lymphoblastic leukemia (ALL) and acute myelogenous leukemia (AML) was examined to determine their potential value in monitoring disease activity in adult acute leukemia. (Heldman et al., Blood 61, 1983). Excretion of $m^1I$ for the patients evaluated is shown in FIG. 5. The dashed lines represent the median values. Normal controls had a median excretion level of 1.22 nmole/$\mu$ mole creatinine. Median excretion of $m^1I$ by patients with ALL at initial diagnosis (Dx) or in relapse (Rel) was 4.27; median excretion of $m^1I$ by patients with ALL in complete remission (CR) was 2.08. Patients with ALL had a significantly elevated excretion compared to the control group ($p<0.01$). In addition, excretion of $m^1I$ by patients with ALL at initial diagnosis or in relapse was significantly greater than excretion by those in remission ($p<0.01$).

Median excretion of $m^1I$ by patients with AML was 2.68 nmole/$\mu$ mole creatinine at initial diagnosis or in relapse, 2.03 in partial remission (PR), and 2.30 in complete remission (FIG. 5). There were no significant differences in excretion among the groups of patients with AML. However, patients with AML had a significant elevation of $m^1I$ excretion compared to the control group ($p<0.01$). Finally, excretion of $m^1I$ by patients with ALL at initial diagnosis or in relapse was significantly higher than that observed in patients with AML at initial diagnosis or in relapse ($p<0.01$).

The group of patients with ALL at initial diagnosis or in relapse had a median percentage of immature cells in the bone marrow aspirate of 71% (range 60%-90%) and a median absolute blast cell count in the peripheral blood of 2300 blasts (range 130-97,000). Likewise, patients with AML at diagnosis or relapse had a median of 62% (range 37%-92%) immature cells in the bone marrow aspirate and a median of 800 blasts (range 30-73,000) in the peripheral blood. There were no significant differences between these two groups of patients in terms of percentage of immature cells in the bone marrow aspirate of the absolute blast count in the peripheral blood ($p>0.05$ for both).

Patients with ALL at initial diagnosis or in relapse had significantly higher concentrations of 1-methylinosine and $N^2$, $N^2$-dimethylguanosine in their urine compared to patients in remission. Heldman, et al., Blood 61, (1983). Referring now to FIG. 6, the control values for urinary excretion of pseudouridine, 1-methyladenosine, PCNR [a metabolite of NAD], 1-methylinosine, 1-methylguanosine, adenosine, and $N^2$, $N^2$-dimethylguanosine were determined by quantitating excretion for 24 healthy Caucasians.

Figure 7:
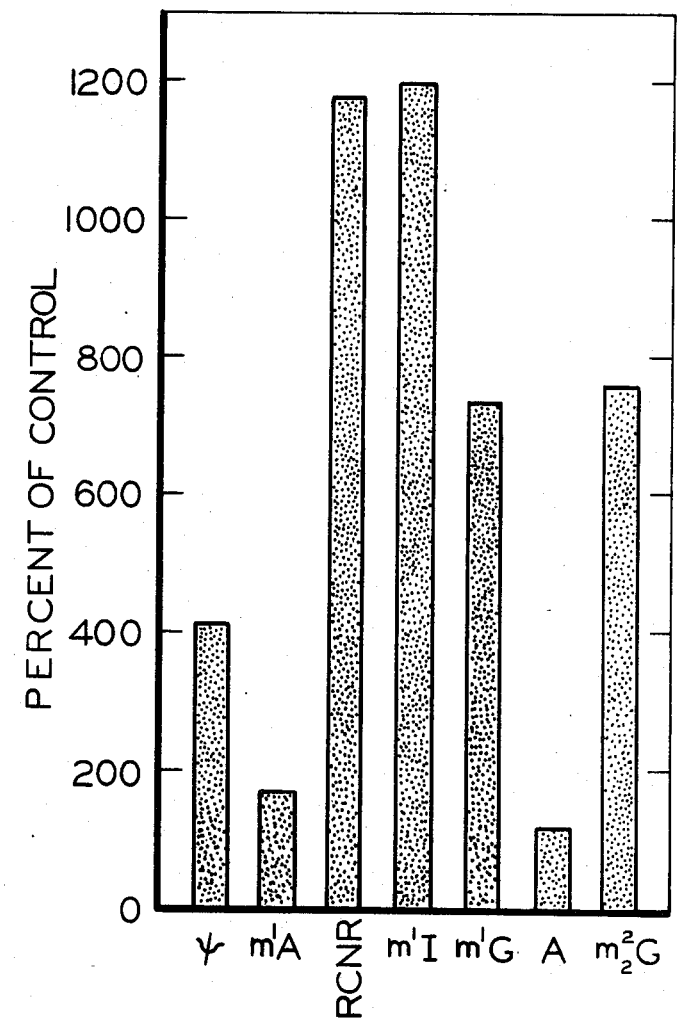
FIG. 7 is a graph showing nucleoside excretion by a patient with chronic myelogenous leukemia (CML) in the blastic phase.

The nucleoside excretion pattern of a 47-year-old female in the blastic phase of CML is shown in FIG. 7. This patient's nucleoside excretion was markedly elevated for all nucleosides except 1-methyladenosine and adenosine. The greatest elevations (approximately 12-fold) were seen in 1-methylinosine and PCNR.

Figure 8:
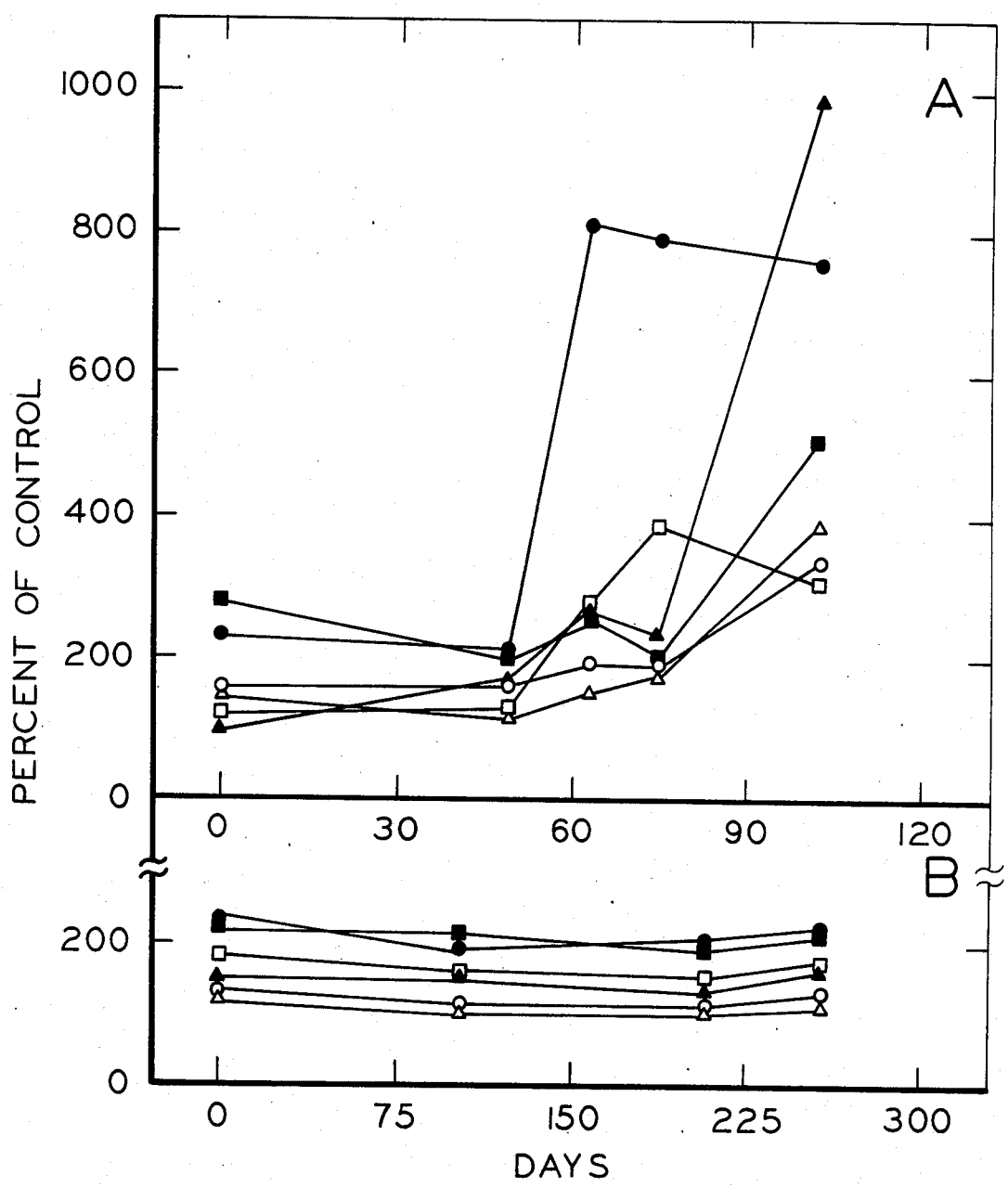
FIG. 8 is a graph serial nucleoside excretion by a patient with CML whose disease accelerated to the blastic phase and by a patient with CML who remained in the stable phase.

Longitudinal studies of nucleoside excretion in two patients with CML are depicted in FIG. 8. Time was based on the number of days after the first urine specimen was collected for evaluation of nucleosides. The nucleosides evaluated are: 1-methylinosine; 1-methylguanosine; $N^2N^2$-dimethylguanosine; O pseudouridine; Δ 1-methyladenosine; PCNR. The nucleoside excretion levels shown in FIG. 8,A, are those of a 46-year-old male whose first urine specimen (day 0) was collected at a time when his peripheral blood and bone marrow demonstrated that his CML was stable. His nucleoside excretion was elevated slightly, with excretion levels ranging from one to three times normal for individual mucleosides. Forty-eight days later, his urinary nucleoside excretion levels were essentially unchanged from their previous values, but shortly thereafter (on day 63), 1-methylinosine showed a significant eightfold increase in excretion. This was followed by a rapid rise in 1-methylguanosine. The increase in 1-methylguanosine in the late phase of the disease seems to be an early indicator of a poor prognosis for a patient. It was not until day 80 that the bone marrow aspirate showed an increase in immature cells, the disease acceleration being in the lymphoid cell line, with lymphoblasts increasing from less than 5% previously to 10% on day 80. The patient was admitted to the hospital in a clinically defined blastic transformation on day 105 (42 days after the increase in 1-methylinosine excretion), at which time all nucleosides were markedly elevated.

In contrast, to the above, FIG. 8,B, illustrates the serial nucleoside excretion levels of a 28-year-old male whose CML remained stable. Four serial specimens were obtained from this patient and his nucleoside excretion was measured consistently at a relatively low level.

Figure 9:
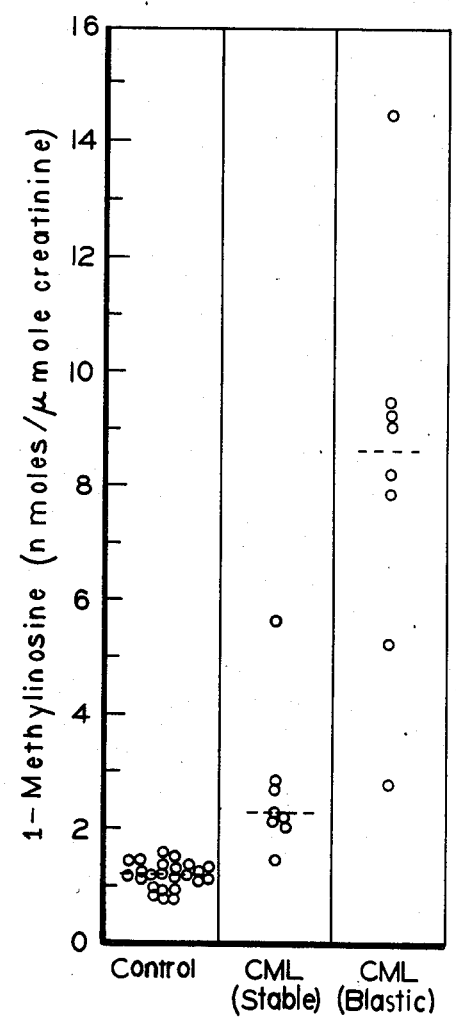
FIG. 9 is a graph showing 1-methylinosine excretion relative to creatinine concentration in control subjects, patients with CML in the stable phase and the blastic phase.

A summary of 1-methylinosine excretion for CML patients evaluated is presented in FIG. 9. The normal controls demonstrated a consistent low level, with a median value of 1.22 nmol/$\mu$mol of creatinine; the median excretion levels for the patients with stable CML and blastic CML were 2.30 and 8.64, respectively. The Wilcoxon rank sum test (Colton, T., Statistics in Medicine, Boston 1974, Little, Brown & Co., pp. 121,351) showed a significant elevation in the excretion of 1-methylinosine by patients in the stable phase compared to the normal controls ($p<0.01$). Patients in the blastic phase had significantly higher levels of excretion than did either the normal controls ($p<0.01$) or the patients in the stable phase ($p<0.01$)

Clearly, 1-methylinosine is useful as a biological marker for cancer. However, the methods utilized are not readily adaptable for routine clinical testing, i.e., the high-performance liquid chromatography technology employed requires expensive instrumentation and only a limited number of samples can be processed and only an extremely small number of facilities enjoy the capability to perform such tests. Other methods of quantitation are required if 1-methylinosine is to be useful for cancer screening. The present invention provides an improved method of quantitation that is readily adaptable for routine clinical testing to detect the presence of very small amounts of excreted elevated levels of 1-methylinosine. Alternatively, 1-methylguanosine may also be detected.

Immunoassays are being increasingly utilized in clinical settings to detect and/or quantitate proteins of interest in biological fluids such as serum and urine. For example, the CEA antigen described previously can be monitored in the blood of cancer patients (if present) by immunoassay techniques (Terry et al., Carcinoembryonic Antigen: characterization and clinical applications. Transplant. Rev. 20: 100-129, 1974).

Radioimmunoassays based on polyclonal antibody techniques have been reported for certain other methylated nucleosides (Levine et al., Serum levels of $N^2$, $N^2$-demethylguanosine and pseudouridine as determined by radioimmunoassay for patients with malignancy. J. Natl. Cancer Inst. 54: 341–343, 1975; Vold, Radioimmunoassays for the modified nucleosides N-[9-(B-D-ribofuranosyl)purin-6-ylcarbamoyl]-L-threonine and 2-methylthioadenosine. Nucleic Acids Res. 7: 193–204, 1979; Vold et al., Urine levels of N-[9-(B-D-ribofuranosyl)purin-6-ylcarbamoyl]-L-threonine, $N^6$-($\Delta^2$-isopentenyl)adenosine, and 2'-0-methylguanosine as determined by radioimmunoassay for normal subjects and cancer patients. Cancer Res. 42: 5265–5269, 1982). In addition, a radioimmunoassay based on monoclonal antibody techniques was recently described for the modified nucleoside isopentenyl adenosine and certain of its derivatives (Woodsworth et al., Characterization of monoclonal antibodies specific for isopentenyl adenosine derivatives occurring in transfer RNA. Biochem. Biophys. Res. Commun. 114: 791–796, 1983).

The present invention provides raising antibodies against 1-methylinosine in immunoassay procedures for cancer screening and monitoring. It should be noted that these procedures may be used for the detection of 1-methylguanosine also. The preparation of the 1-methylinosine is as described below.

1-Methylinosine is purified by reversed-phase high-pressure liquid chromatography using an octadecyl column eluted with ammonium phosphate buffer in methanol. 1-Methylinosine-protein conjugates are prepared by periodate oxidation of the 1-methylinosine and coupling reaction with BSA or KLH at a nucleoside/protein ratio of 1:1 (w/w) following the published procedure, Erlanger, B. F. et al., Proc. Natl. Acad. Sci. U.S., 52:68–74 (1964), for the preparation of nucleoside-protein conjugates. The conjugates are dialysed against PBS and analyzed using ultraviolet spectrophotometry. Inouye, H. et. al., Biochem. Biophys. Acta., 240;596–603 (1971).

Two schemes of immunization are used for the preparation of polyclonal antibody directed against 1-methylinosine: (a) three rabbits are immunized with 1-methylinosine-KLH conjugate (5 mg/animal) in 2.5 ml of PBS emulsified in 2.5 ml of complete Freund's adjuvant, by intramuscular injections into the hind limbs and 5–10 other sites (subcutaneous). Four weeks later, the rabbits are boosted by the intravenous injection of 500 ug of nucleoside-protein conjugate per animal in 1 ml PBS at 2 week intervals; (b) a mixture of 500 ug of the 1-methylinosine-KLH conjugate in 0.5 ml of PBS and 0.5 ml 1-methylinosine-KLH conjugate in 0.5 ml of PBS and 0.5 ml aluminum hydroxide is stirred for 1 hour at 4° C. and emulsified in 1 ml of complete Freund's adjuvant. Three rabbits are immunized by intramuscular injections into the hind limbs and into 25–30 intracutaneous sites (neck and back). Eight weeks later animals are immunized again by the same procedure. After another 8 weeks, the rabbits receive a second booster by intramuscular injection of 500 ug of conjugate in 1 ml PBS emulsified in 1 ml incomplete Freund's adjuvant. Blood samples are collected by ear puncture for testing for the presence of antibody in the blood. The blood is tested after clotting by the ELISA method described below for antibody activity. The blood of rabbits shown positive for 1-methylinosine antibody is collected by cardiac puncture, clotted, centrifuged and the resultant serum is stored at 4° C. in suspension form by precipitating with ammonium sulfate to 40% saturation. The antibody is reconstituted by centrifugation of a suitable aliquot of the suspension, dissolving the pellet in PBS followed by dialysis in PBS containing 0.5% merthiolate. Antinucleoside-antibody activity is tested using ELISA and RIA as described below. The antibody prepared in this manner does not show any measurable loss of its binding properties upon storage.

As a preferred alternative to the aforementioned procedures for producing the polyclonal antibody, a monoclonal antibody preparation may be used. Female BALB/c mice 8 weeks old are given a primary intraperitoneal injection of approximately 100 ug 1-methylinosine-KLH conjugate mixed with killed *Bordetella pertussis* organisms used to stimulate the immune system. Each mouse is then given 3 intraperitoneal injections 2 weeks apart, each consisting of approximately 10 ug 1-methylinosine-KLH conjugate emulsified with incomplete Freud's adjuvant in 0.5 ml. Blood samples are removed from the tail vein at 4 and 6 weeks after the second injection and the serum is isolated from the blood and assayed by the ELISA procedure described below for antibody activity. The mice are given a final booster immunization of 10 ug conjugate and killed three days later. The spleens of each animal are asceptically removed and mechanically dissociated by passage through a sterile steel mesh (100 um). $10^7$ mouse myeloma P3X63 NS-1 cells (6-thioguanine resistant cells obtained from the Human Genetic Mutant Cell Repository), grown as suspension cultures are fused with $10^8$ spleen cells. The fusion of the cells are done by adding 50%, polyethylene glycol and are stirred gently for 1 minute. Over the next 2-3 minutes, 9 ml of serum free mMEM is added with gentle shaking of the tubes. The cells are pelleted by centrifugation and resuspended into 20 ml mMEM 10% FCS (fetal calf serum) and incubated 24 hours at 37° C. The next day the cells are diluted to $1 \times 10^6$ cells per ml with hypoxanthine, aminopterin, thymidine (HAT) containing medium and distributed in 0.1 ml aliquots into wells of Costar multiwell plates. 50 ul of fresh HAT medium is substituted to each well on every 2 days through day 14. Isolated colonies are visible in 1–2 weeks, at which time the medium is tested by ELISA for anti-nucleoside activity. Cells from positive hybridoma containing wells are cloned by the limiting dilution procedure, Oi, V.T. et al., *Selected Methods in Cellular Immunology*, Mishell, B.B., et al., Eds., pp. 351–372, Freeman, San Francisco (1980), so that 0.5, 1.0 or 5.0 cells are added to each well of the 96-well plate. Mouse spleen feeder cells are isolated from the spleens of nonimmunized 14 day old BALB/c mice. Approximately $10^7$ cells/ml are added into each well. After 7 days the wells are examined for single viable clones that are then tested for specific antinucleoside antibody activity using the ELISA and RIA methods described below. Stable positive clones are expanded through 1 to 50 ml cultures at a seeding density of $1 \times 10^5$ cells/ml. Cells are allowed to grow two weeks in mMEM before harvesting the supernatant containing antibody. The antibody containing medium is aliquoted into 1 ml fractions and stored at −70° C. without loss of antibody activity.

The antibody thus prepared may be used in an ELISA assay. The preferred technique for carrying out such an assay with the instant antibody is described herein.

The ELISA is performed in 96 well flexible microtiter plates (type 3912, Becton-Dickinson) and used for detection of antibody activity. The wells of the plates are filled with 0.1 ml of an appropriate concentration of coating solution (1-methylinosine-BSA conjugate in PBS) and incubated for 1 h at 37° C. or dried completely by overnight incubation at 37° C. The wells are washed 3 times with PBS-tween. Remaining free binding sites on the plastic surface are saturated by filling the wells with 1% BSA and incubating at 37° C. for 1 hour. The protein solution is washed out and wells incubated for 1 hour at 37° C., with 0.1 ml of an appropriate dilution of antibody in PBS-tween. The antibody is removed and wells are washed three times. 0.1 ml of goat anti-rabbit or anti-mouse IgG-alkaline phosphatase conjugate diluted 1:1000 in PBS-Tween, is added. After 1 hour incubation at 37° C., the wells are washed three times with PBS-tween and two times with 0.1 M DEA Buffer, pH 9.6.

The presence of 1-methylinosine in test body fluids such as, for example, urine, amniotic fluid, ascites fluid, or serum, is determined by the competition for antibody binding sites on the plastic surface, to which has been bound 1-methylinosine-BSA conjugate. 1-Methylinosine in the test fluid will bind the anti-1-methylinosine antibody that would otherwise bind to 1-methylinosine-BSA conjugate bound to the plastic surface.

The antibody-bound alkaline phosphatase is assayed as follows: A sample (10–50 ul) of test fluid is mixed with antibody and incubated for 1 hour at 37° C. This sample is then added to the well and incubated for 1 hour at 37° C. The wells are washed three times with PBS-tween and two times with 0.1M DEA buffer, pH 9.6.

A 0.1 ml solution of p-nitrophenyl phosphate (1 mg/ml) in 1M DEA buffer, pH 9.6, 1 mM $MgCl_2$ is added to each well. After 1 hour incubation period the reaction is stopped by the addition of 0.01 ml DEA stop buffer. The absorbance at 405 nm of the product formed is measured directly in the wells using a EIA reader. The samples are run in duplicates and the values obtained are within 2–4% (S.D.) of the mean. During the various incubation steps described above, except for the drying step, the plates are properly sealed with parafilm and a humidified atmosphere is used to prevent evaporation and non-specific binding of the reagents to the plastic surface by drying.

The readings are compared to wells incubated with control fluid and without test fluid. The percent of inhibition of the antigen-antibody binding gives a quantitive estimation of 1-methylinosine present in the test fluid. The value obtained in test fluid is compared with values obtained by adding known amounts of 1-methylinosine to calibration standards.

A second procedure for the detection of 1-methylinosine by ELISA, is by absorbing the antibody to the surface of the plastic wells by drying overnight at 37° C. The wells are washed three times with a solution of PBS-Tween. The remaining free binding sites on the plastic surface are saturated by filling the wells with 1% BSA and incubating at 37° C. for 1 hour. The protein solution is washed out and the wells are incubated for 1 hour at 37° C. with the fluid sample adjusted to a pH of 7.2. The fluid sample is removed and the wells are washed three times with PBS-Tween. A 0.1 ml sample of the antibody to 1-methylinosine coupled to alkaline phosphatase is incubated for 1 hour at 37° C. The antibody is coupled to alkaline phosphatase by incubating the antibody and alkaline phosphatase in 0.5% glutaraldehyde with stirring for 1 hour. The reaction is terminated by dialysis against 0.1M $(NH_4)_2CO_3$ for 3–5 hours and then PBS overnight at 4° C. The sample is centrifuged to remove any precipitate and chromatographed on a Sepharose 2B column with 0.05M phosphate, pH 7.5. The resultant antinucleoside-alkaline phosphatase is tested for antibody and enzyme activity. The wells are again washed three times with the PBS-Tween solution and two times with 0.1M DEA stop buffer, pH 9.6. A 0.1 ml solution of p-nitrophenyl phosphate (1 mg/ml) in 1M DEA buffer, pH 9.6, 1 mM $MgCl_2$ is added to each well. After 1 hour incubation period the reaction is stopped by the addition of 0.01 ml DEA stop buffer. The absorbance at 405 nm of the product formed is measured directly in the wells using a EIA reader. The samples are run in duplicates and the values obtained are within 2–4% (S.D.) of the mean. During the various incubation steps described above, except for the drying step, the plates are sealed with parafilm and a humidified atmosphere is used to prevent evaporation and non-specific binding of the reagents to the plastic surface by drying.

Appropriate standards are used with known quantities of 1-methylinosine dissolved in control fluid. This is done so as to make a quantitiative determination of the amount of 1-methylinosine in the test fluid.

For Ultrasensitive Enzyme Linked Radioimmune Assay (USERIA) detection of antibody binding antinucleoside, 0.1 ml (10 pmol) of [3,5-$^3$H] p-nitrophenyl phosphate (sp. act., 29.9 ci/mmole; NEN) in 20 mM DEA buffer, pH 9.6, 5 mM $MgCl_2$ is added to each well of the 96 well plate described above for ELISA and incubated for 1 hour at 37° C. in a humidified chamber. The reaction is stopped by transferring 20 ul aliquots from the well into a vial containing 2 ml PBS. 3.5 ml of scintillation cocktail (BBOT in toluene) is added and the mixture shaken. The radiometric determination of the vials gives radioactivity counts only due to the formation of p-nitrophenol which is soluble in the organic phase of the liquid scintillation cocktail. The unhydrolysed substrate is only soluble in aqueous phase and does not contribute to the radioactive counts detected by the liquid scintillation spectrophotometer. Thus the use of this substrate eliminates the use of tedious separations by column chromatography or direct addition of resin to the wells for separation. During the various incubation steps described above, except for the drying step, the plates are properly sealed with parafilm and the humidified atmosphere is used to prevent evaporation and non-specific binding of the reagents to the plastic surface by drying.

Appropriate standards are used with known quantities of 1-methylinosine dissolved in control fluid. This is done so as to make a quantitative determination of the amount of 1-methylinosine in the test fluid.

The Radioimmunoassay (RIA) is carred out by a modification of Farr assay. Farr, R. S., J. Infec. Dis. 103: 239–262 (1958). Each sample contained in a total volume of 0.2 ml of buffer [tris/Nacl with 1% BSA (w/v) and 0.1% normal rabbit IgG (w/v)], 4,000 dpm (0.06 pmol) of tracer (1-[G-$^3$H]-methylinosine), antinucleoside serum and various amounts of urine. After incubation for 1 hour at 37° C., 0.2 ml of a saturated ammonium sulfate solution (pH 7.0) is added. The tubes are held in an ice bath for 30 minutes and centrifuged for 10 minutes at 9,000 g. The radioactivity in 0.3 ml of supernatant solution is measured in 5 ml scintillation fluid miscible with an aqueous sample, in a liquid scintillation spectrometer. The degree of inhibition of tracer antibody binding is calculated by the formula: $[(dmp_1 - dpm_2)/(dpm_3 - dpm_2)] \times 100$. $Dpm_1$ is dpm in the supernatant of inhibitor containing sample, $dpm_2$ is the dpm in the supernatant of the sample without inhibitor (0% inhibition), and $dpm_3$ is the dpm of the sample without antibodies (100% inhibition). Samples are run in triplicates and inhibition values are within ±4% of the mean. The affinity constant for various antibodies are determined as described for other antinucleoside antibodies, (Muller, R., J. Immunol Meth., 34: 345-352 (1980).

Appropriate standards are used with known quantities of 1-methylinosine dissolved in control fluid. This is done so as to make a quantitative determination of the amount of 1-methylinosine in the test fluid.

It will be apparent to those skilled in the art that numerous changes and modifications can be made in the preferred embodiments of the invention described above without departing from the scope of the invention. Accordingly, the whole of the foregoing description is to be construed in an illustrative and not in a limitative sense, the scope of the invention being defined solely by the appended claims.

We claim:

1. A method for the early detection of or relapse of leukemia in a human by determining the presence of elevated levels of the 1-methylinosine modified nucleoside using antibodies specific to the modified nucleoside comprising the following steps:
   producing a polyclonal or monoclonal antibody specific to said modified 1-methylinosine nucleoside component, said modified 1-methylinosine nucleoside component being present in elevated levels in said human having cancer;
   admixing said antibody with a body fluid drawn from said human, said body fluid having a quantity of said modified 1-methylinosine nucleoside component therein, said antibody reacting with said modified 1-methylinosine nucleoside component present in said body fluid to form a modified 1-methylinosine nucleoside antibody complex;
   thereafter determining the presence of elevated levels of said modified 1-methylinosine nucleoside component in said admixture by observing the presence of said modified 1-methylinosine nucleoside-antibody complex present in said body fluid.

2. The method according to claim 1, wherein the modified nucleoside component has the formula:

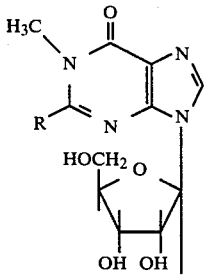

wherein R is H or $NH_2$.

3. The method according to claim 1, wherein said body fluid comprises urine.

4. The method according to claim 1, wherein said body fluid comprises blood serum.

5. The method according to claim 1, wherein said body fluid comprises amniotic fluid.

6. The method according to claim 1, wherein said body fluid comprises ascites fluid.

7. The method according to claim 1, wherein said modified nucleoside-antibody complex is detected by means of an enzyme label.

8. The method according the claim 1, wherein said modified nucleoside-antibody complex is detected by means of an ultrasensitive enzyme label.

9. The method according to claim 1, wherein said modified nucleoside-antibody complex is detected by means of a radioactive enzyme label.

10. The method according to claim 1, wherein said antibody is produced by;
    introducing into the bloodstream of a mouse a nucleoside preparation having said modified nucleoside component, said nucleoside preparation including approximately 100 ug. 1-methylinosine-KLH conjugate;
    further injecting said mouse with approximately 10 ug. 1-methylinosine-KLH conjugate at approximately 2 week intervals 3 times;
    removing a blood sample from the tail vein of said mouse at approximately 4 and 6 weeks after said second injection, isolating serum from said blood sample, assaying said serum for the determination of antibody activity;
    removing the spleen from said mouse;
    fusing removed spleen cells with mouse myeloma cells and culturing resultant hybridoma cells;
    selecting from said cultured hybridoma cells at least one clone capable of producing said antibody; and,
    harvesting said antibody from said clone culture.

11. The method according to claim 10 wherein said culturing of said hybridoma cells includes diluting said cells with a medium containing hypoxanthine, aminopterin and thymidine, and further including the step of substituting said medium with fresh medium approximately every 2 days through day 14.

12. The method according to claim 1, wherein said polyclonal antibody is produced by:
    introducing into the bloodstream of a mammal a nucleoside preparation having said modified nucleoside component;
    allowing said preparation to remain in said bloodstream of said mammal for a predetermined time period;
    removing blood from said mammal;
    preparing serum from said blood; and,
    assaying said serum for determination of antibody activity.

13. A method according to claim 12, wherein said nucleoside preparation is introduced into said bloodstream of said mammal together with an immunostimulating adjuvant.

14. The method according to claim 12, wherein said mammal is a rabbit.

15. A method of detecting the presence of a modified 1-methylinosine nucleoside component, said modified 1-methylinosine nucleoside component being present in elevated levels in a human having leukemia, said method comprising the following steps:
    producing a monoclonal antibody specific to said modified 1-methylinosine nucleoside component, said antibody being produced by:
    (a) introducing into the bloodstream of a mouse a nucleoside preparation, said nucleoside preparation including a nucleoside-protein conjugate;
    (b) thereafter injecting said mouse with said conjugate at predetermined intervals of time such that said mouse produces antibodies specific to said modified 1-methylinosine nucleoside component;

(c) thereafter removing a blood sample from said mouse, isolating serum from said blood sample, and assaying said serum for determination of antibody activity;

(d) removing the spleen from said mouse;

(e) fusing removed spleen cells with mouse myeloma cells and culturing resultant hybridoma cells;

(f) selecting from said cultured hybridoma cells at least one clone capable of producing said antibody; and, (g) harvesting said antibody from said clone culture; thereafter admixing said harvested antibody with a test sample drawn from said human, said antibody reacting with said modified 1-methylinosine nucleoside component present in said test sample to form a modified 1-methylinosine nucleoside-antibody complex;

thereafter detecting the presence of elevated levels of said modified 1-methylinosine nucleoside component in said admixture by observing said modified 1-methylinosine nucleoside-antibody complex present in said test sample.

16. A method of monitoring the treatment of cancer in patients excreting elevated levels of said modified nucleoside by using the method of claim 1 wherein multiple determinations of said elevated levels of said modified nucleoside are made and compared to a standard.

17. A method of monitoring the treatment of cancer in patients excreting elevated levels of said modified nucleoside by using the method of claim 13 wherein multiple determinations of said elevated levels of said modified nucleoside are made and compared to a standard.

18. A method of monitoring the treatment of cancer in patients excreting elevated levels of said modified nucleoside by using the method of claim 12 wherein multiple determinations of said elevated levels of said modified nucleoside are made and compared to a standard.

19. A method of monitoring the treatment of cancer in patients excreting elevated levels of said modified nucleoside by using the method of claim 15 wherein multiple determinations of said elevated levels of said modified nucleoside are made and compared to a standard.

* * * * *

UNITED STATES PATENT AND TRADEMARK OFFICE
CERTIFICATE OF CORRECTION

PATENT NO. : 4,687,733

DATED : August 18, 1987

INVENTOR(S) : Trewyn et al.

It is certified that error appears in the above—identified patent and that said Letters Patent is hereby corrected as shown below:

Column 5, line 64, before 1-methylinosine insert -- ● --;

Column 5, line 64, before 1- insert -- ▲ --;

Column 5, line 65 before $N^2N^2$-dimethylguanosine insert -- ■ --;

Column 5, line 66 before PCNR insert -- ☐ --;

Column 6, line 5 delete "mucleosides" and insert --nucleosides--.

Signed and Sealed this

Nineteenth Day of April, 1988

Attest:

DONALD J. QUIGG

*Attesting Officer*   *Commissioner of Patents and Trademarks*